(12) United States Patent
Sharratt et al.

(10) Patent No.: US 7,019,178 B2
(45) Date of Patent: Mar. 28, 2006

(54) PROCESS FOR THE PURIFICATION OF FLUOROMETHYL HEXAFLUOROISOPROPYL ETHER

(75) Inventors: Andrew P. Sharratt, Cheshire (GB); Stuart Corr, Cheshire (GB)

(73) Assignee: Ineos Fluor Holdings Limited, Runcorn (GB)

( * ) Notice: Subject to any disclaimer, the term of this patent is extended or adjusted under 35 U.S.C. 154(b) by 0 days.

(21) Appl. No.: 10/451,265

(22) PCT Filed: Dec. 21, 2001

(86) PCT No.: PCT/GB01/05727

§ 371 (c)(1),
(2), (4) Date: Dec. 8, 2003

(87) PCT Pub. No.: WO02/50004

PCT Pub. Date: Jun. 27, 2002

(65) Prior Publication Data

US 2005/0261526 A1 Nov. 24, 2005

(30) Foreign Application Priority Data

Dec. 21, 2000 (GB) .................................. 0031303

(51) Int. Cl.
*C07C 41/34* (2006.01)

(52) U.S. Cl. ...................................... 568/682; 568/683
(58) Field of Classification Search ................ 568/682, 568/683

See application file for complete search history.

(56) References Cited

U.S. PATENT DOCUMENTS

| | | | | |
|---|---|---|---|---|
| 3,085,379 A | * | 4/1963 | Kiyonaga et al. | ............... 95/96 |
| 5,352,785 A | * | 10/1994 | Herzberg et al. | ........... 544/178 |
| 5,679,576 A | * | 10/1997 | Kawai et al. | .................. 436/55 |
| 5,763,684 A | * | 6/1998 | Kawai et al. | ................ 568/682 |
| 6,002,133 A | * | 12/1999 | Nelson et al. | ............... 250/343 |
| 6,443,150 B1 | * | 9/2002 | Pessala et al. | ......... 128/203.14 |
| 2003/0180209 A1 | * | 9/2003 | Gordeev et al. | ........ 423/445 R |

* cited by examiner

*Primary Examiner*—Rosalynd Keys
(74) *Attorney, Agent, or Firm*—Morgan Lewis & Bockius LLP

(57) ABSTRACT

A process for the purification of fluoromethyl hexafluoroisopropyl ether involving contacting a crude composition containing impure fluoromethyl hexafluoroisopropyl ether with an adsorbent having pores with a range of pore sizes whereby the difference between the smallest and largest pore size is at least 1 nm. The adsorbent suitably is a form of silica, alumina, or carbon.

16 Claims, No Drawings

PROCESS FOR THE PURIFICATION OF FLUOROMETHYL HEXAFLUOROISOPROPYL ETHER

This invention relates to a process for the purification of ether of formula $CH_2FOCH(CF_3)_2$ which has anaesthetic properties and is known as "Sevoflurane".

It is known that Sevoflurane may be produced by the reaction of formaldehyde, hydrogen fluoride and hexafluoroisopropyl alcohol $(CF_3)_2CHOH$ (HFIP). For example, U.S. Pat. No. 4,250,334 describes a process in which hexafluoroisopropyl alcohol is added to a mixture of a stoichiometric excess of paraformaldehyde and hydrogen fluoride plus sufficient sulphuric acid to sequester most of the water formed. It is also known to produce Sevoflurane from bis (fluoromethyl) ether and hexafluoroisopropyl alcohol. WO97/25303 describes a process for the production of Sevoflurane in which essentially pure bis(fluoromethyl) ether is reacted with hexafluoroisopropyl alcohol.

However, in producing Sevoflurane, by-products, unused reactants and other impurities typically are found in the reaction mixture. The type and level of any impurity depends on the process chemistry and conditions employed to produce Sevoflurane but typical impurities may include one or more of hydrogen fluoride, formaldehyde, trioxane, hexafluoroisopropanol (HFIP), bis(fluoromethyl) ether (BFME), polyethers, and fluorinated olefins, for example pentafluoroisopropenyl fluoromethyl ether (PFIE). In addition, Sevoflurane may also undergo some decomposition either during processing or when stored for example in glass bottles prior to use.

It is necessary to remove or at least reduce the level of some or all of these impurities from Sevoflurane prior to use due to the stringent requirements of purity for medical use.

WO 98/32430 discloses that decomposition is thought to occur when Sevoflurane comes into contact with Lewis acids. Also, the presence of hydrogen fluoride or its formation as a decomposition product may exacerbate decomposition in glass due to the etching effect of hydrogen fluoride on glass which releases further Lewis acid and promotes further decomposition. However, U.S. Pat. No. 5,684,210 discloses a process for purifying Sevoflurane in which the presence of BFME impurity has been reduced by contacting the product with a Lewis acid, a Bronsted acid or an acidic species fixed on a resin.

Especial difficulties arise in relation to impurities which have similar physical properties, for example boiling point, to the desired product as this may preclude or render difficult certain types of separation technique, for example distillation. HFIP and PFIE are both toxic and have similar boiling points to Sevoflurane and separation by distillation may present practical difficulties. Acidic species, for example hydrogen fluoride and HFIP, may be removed by washing the product with an alkaline solution. WO 99/44978 describes a process to remove HFIP from crude Sevoflurane which involves employing an aqueous alkaline wash. However, washing with alkaline solution may remove acidic impurities but may also cause the formation of olefinic impurities for example PFIE which may be difficult to separate from Sevoflurane in an efficient and economically viable manner. Removal of olefinic impurities using an amine is described in U.S. Pat. No. 4,328,376 but this may lead to undesirable odour in the purified product.

EP-A-835858 describes a purification process in which a mixture of Sevoflurane and BFME are contacted with a zeolite to remove BFME. Zeolitic materials typically contain a large number of active adsorption sites within the porous structure of the zeolite. A large proportion of the adsorption sites in the zeolite are accessed by the molecule to be adsorbed passing through pores of a certain size in the surface of the zeolite. Whether a molecule may be adsorbed accordingly depends at least in part on the size of the molecule and may lead to molecules of a comparable size being adsorbed without significant selection of one species over another. Adsorption into a zeolite may be considered, in large part, to be a physical effect based on the size and shape of the species to be adsorbed.

A range of different purification processes have been developed to purify Sevoflurane but due to the number of possible impurities, some purification measures also appear to introduce other drawbacks requiring further treatment and so leading to complexity and increased process cost.

It has now been found that crude Sevoflurane containing Sevoflurane and one or more impurities may be treated to remove a range of impurities in an efficient manner by contacting the crude Sevoflurane with an adsorbent having a wide pore size distribution and, preferably, which selectively adsorbs a material by chemical rather than physical means.

According to the present invention there is provided a process for the purification of fluoromethyl hexafluoroisopropyl ether which comprises contacting a crude composition comprising fluoromethyl hexafluoroisopropyl ether and at least one impurity with an adsorbent having pores with a range of pore sizes whereby at least one impurity is removed from the crude composition and recovering the crude composition depleted in the said impurity.

Advantageously, the invention permits a range of impurities to be removed from Sevoflurane simultaneously. The range of pore sizes distribution of the adsorbent allows the components of the crude composition to come into contact with the adsorbent sites whereby at least one impurity in the crude composition is adsorbed. It is believed that the adsorbent may be able to preferentially adsorb one component rather than another due to selective chemisorption. Use of an adsorbent as described suitably provides the practical advantage of enabling crude Sevoflurane to be purified in a single purification step depending on the impurities in the crude composition and does not introduce further complications which require additional downstream processing. If desired, additional purification techniques known in the art may be employed in addition to that of the present invention either upstream or downstream of contacting with the absorbent.

Suitably the pores in the adsorbent have a pore size distribution of at least 1 nm and preferably at least 2 nm. Thus the adsorbent contains pores across a range from pore size "a" to pore size "b" in which the difference between "a" and "b" is at least 1 and preferably at least 2 nm.

Preferably at least some of the pores in the adsorbent have a pore size across a range of 1.5 to 2.5 nm and desirably across a range of 1 to 3 nm. Desirably at least 50% by volume of the pores have a pore size across a range of 1 to 3 nm.

Further, the adsorbent suitably comprises micropores having a pore size across the range 1 to 3 nm and macropores having a pore size across the range 3 to 10000 nm.

The adsorbents suitable for use in the process of the present invention are distinguished from zeolites in that, as a bulk material, the adsorbent has pores of a size across a broad range so that a plot of distribution of pore sizes suitably provide a "bell-shaped" plot whereas zeolites typically have pores of a size across a very narrow range and a plot of distribution of pore sizes on a comparable scale typically provides a "needle-shaped" plot. It is the range of pore sizes in the adsorbents suitable for use in the present process wich enable components of comparable molecular sizes to be separated.

The adsorbent may comprise a form of silica, alumina, carbon or mixtures thereof. It is especially preferred that the adsorbent be in activated form. Carbon, desirably in activated form as activated carbon or activated charcoal is especially preferred. The adsorbent may be acidic, basic or neutral. If desired, the adsorbent may additionally comprise a zeolite.

It has further been found that a crude Sevoflurane composition may be treated to remove at least one impurity by contacting with an adsorbent comprising carbon.

In a preferred embodiment of the invention, there is provided a process for the purification of fluoromethyl hexafluoroisopropyl ether which comprises contacting a crude composition comprising fluoromethyl hexafluoroisopropyl ether and at least one impurity with an adsorbent having a pore size distribution of at least 1 nm and preferably at least 2 nm and at least 50% by volume of the pores, have a pore size across a range of 1 to 3 nm.

It has been found that carbon in various forms is especially advantageous due to the preferential adsorption of impurities in a crude Sevoflurane composition and especially the preferential adsorption of olefinic impurities, for example pentafluoroisopropenyl fluoromethyl ether (PFIE). In addition, Lewis acids employed as adsorbents may disadvantageously promote the degradation of Sevoflurane whereas carbon adsorbents do not introduce such drawbacks.

It is believed that the preferential adsorption takes place due to selective chemisorption arising because of the different chemical structures of the components to in the crude composition.

Where a mixture of adsorbent materials is employed, they may be employed as separate adsorption materials with which the crude Sevoflurane composition is contacted sequentially or as a mixture and preferably a generally homogeneous mixture. If the purification process is operated continuously, the adsorbent suitably is arranged as an adsorbent bed through which the crude composition is passed and the bed may comprise, in the case of a mixture of adsorbent materials a homogeneous bed of the mixed adsorbents or a multi-layered bed in which different layers are made primarily from different adsorbent materials. In a batch process, the adsorbent materials may be added together to the batch process or sequentially.

The process according to the invention may be operated as a part of a production process in which crude Sevoflurane is manufactured and passed to the purification step or, as desired, is also applicable to the treatment of Sevoflurane which has been stored for a period of time and contains sufficient impurities not to meet the desired specification for instance, for medical use. Sevoflurane which has been stored and contains impurities may, in the context of the present invention, be considered as crude Sevoflurane even if it has previously been subjected to a purification process.

The crude Sevoflurane composition contains one or more impurities which may include one or more of hydrogen fluoride, formaldehyde, trioxane, paraformaldehyde, hexafluoroisopropanol (HFIP), bis(fluoromethyl) ether (BFME), a polyether, and a fluorinated olefin, for example pentafluoroisopropenyl fluoromethyl ether (PFIE). The invention is especially beneficial in removing olefinic impurities from the crude Sevoflurane.

In a further aspect, the invention provides for use of an adsorbent having a pore size distribution of at least 1 nm preferably comprising carbon in the purification of a crude composition comprising fluoromethyl hexafluoroisopropyl ether and an olefinic impurity, preferably pentafluoroisopropenyl fluoromethyl ether (PFIE), to produced purified fluoromethyl hexafluoroisopropyl ether.

The quantity of adsorbent employed may be selected according to the level of impurities in the crude Sevoflurane. The level of adsorbent is not especially critical although efficacy of purification and cost are factors which may affect the specific level of adsorbent used. By way of guidance the level of adsorbent may be up to 100% w/w of Sevoflurane in the crude composition although a level of 0.1 to 50% by weight, preferably from 1 to 50% by weight or even 2 to 30% by weight of the quantity of Sevoflurane in the crude Sevoflurane mixture.

The crude Sevoflurane is suitably contacted with the adsorbent for a period sufficient to remove or reduce impurities to a pre-determined level according to the manner in which the process is operated. Where the process is conducted in the gaseous phase, the contact time with the adsorbent is suitably of the order of seconds, preferably 1 to 120 seconds and more preferably 2 to 60 seconds. For a continuous liquid phase process, the contact time suitably is of the order of 1 to 45 minutes and preferably 2 to 30 minutes. In a batch liquid phase process the contact time may be up to 24 hours, preferably 1 to 10 hours and especially 2 to 6 hours. The temperature at which the crude Sevoflurane and carbon are contacted may be elevated or below ambient but, preferably is at ambient temperature to avoid introducing complexity into that part of the process.

The crude Sevoflurane may be contacted with the adsorbent in batch-wise fashion or in a continuous process as desired.

In a preferred embodiment, the invention provides a process which comprises producing a crude composition comprising fluoromethyl hexafluoroisopropyl ether and at least one impurity, contacting the crude composition with an absorbent comprising carbon so as to remove at least some of the at least one impurity from the crude composition, suitably to achieve a pre-determined specification, and recovering fluoromethyl hexafluoroisopropyl ether from the crude composition.

The crude composition comprising Sevoflurane may be produced by any known route for example by reacting formaldehyde whether as such or in another known form, for example a polymeric form of formaldehyde such as paraformaldehyde or trioxane, with hydrogen fluoride and HFIP. Preferably however, the crude Sevoflurane is produced by reacting BFME with HFIP. Optimally, the crude composition is produced in the presence of an acid, preferably a Bronsted or Lewis acid, for example sulphuric acid.

The reaction between the bis(fluoromethyl) ether and the hexafluoroisopropyl alcohol is conveniently carried out at a temperature of less than 50° C., preferably 10 to 50° C. especially 10 to 35° C. Suitably the reaction is carried out at atmospheric pressure, although if desired subatmospheric or superatmospheric pressure. The reaction is preferably carried out in the presence of an acid preferably a Lewis or Bronsted acid for example sulphuric acid.

If used, BFME may be employed as is without purification and advantageously enables the operation of an integrated process including the production of BFME and its direct use as a feedstock to produce Sevoflurane. Alternatively, BFME may be treated so as to purify it partly or wholly prior to use in the production of Sevoflurane. If desired, bis(fluoromethyl) ether may be separated from the reaction mixture and treated to produce essentially pure bis(fluoromethyl) ether which may then be reacted with hexafluoroisopropyl alcohol to produce fluoromethyl-hexafluoroisopropylether. Formaldehyde and/or hydrogen fluoride may be fed to the process of the invention in addition to BFME and HFIP as desired.

The process for the production of the crude composition may be operated as a batch or continuous process or a combination thereof but is preferably operated as a batch process.

The bis(fluoromethyl) ether may be produced by reaction of formaldehyde or a known form of it with hydrogen fluoride. Any of the known methods for production of the bis(fluoromethyl) ether may be employed as the ether formation step. The production of bis(fluoromethyl) ether from formaldehyde and hydrogen fluoride is described, for example, in EP-A-518506 and in WO 93/10070, WO 93/12057 and WO 93/22265, for example. The disclosures of these publications are incorporated herein by reference. The ether production process described in WO 93/10070 is especially preferred and comprises reacting formaldehyde with hydrogen fluoride in a reaction-distillation column from which the ether is withdrawn in essentially pure form and in particular essentially free from water.

The invention is illustrated but in now way limited by the following Examples

EXAMPLE

Crude Sevoflurane (2.0 ml) containing PFIE at a level of about 300 ppm by weight and other trace impurities was mixed with activated carbon (0.20 g) (Carbon Norit RO 1/16 inch (1.56 mm) extrudates) for 2 hours at ambient temperature and pressure. The treated product was then analysed by gas chromatography and compared with the analysis of the untreated product. The carbon treatment successfully reduced the level of PFIE by at least 75% and significantly reduced the level of other impurities.

What is claimed is:

1. A process for the purification of fluoromethyl hexafluoroisopropyl ether which comprises contacting a crude composition comprising fluoromethyl hexafluoroisopropyl ether and at least one impurity selected from hydrogen fluoride, formaldehyde, paraformaldehyde, trioxane, hexafluoroisopropanol, bis(fluoromethyl) ether, a polyether, and fluorinated olefin with an adsorbent having pores with a range of pore sizes whereby at least one impurity is removed from the crude composition and recovering the crude composition depleted in the said impurity.

2. A process as claim 1 in which the pore size distribution is at least 1 nm.

3. A process as claimed in claim 1 in which the pore size distribution is at least 2 nm.

4. A process as claimed in claim 1 in which at least some of the pores in the adsorbent have a pore size across a range of 1.5 to 2.5 nm.

5. A process as claimed in claim 1 in which at least 50% by volume of the pores have a pore size across a range of 1 to 3 nm.

6. A process as claimed in claim 1 in which the adsorbent comprises micropores having a pore size across the range 1 to 3 nm and macropores having a pore size across the range 3 to 10000 nm.

7. A process as claimed in claim 1 in which the adsorbent is selected from silica, alumina, carbon and mixtures thereof.

8. A process as claimed in claim 7 in which the adsorbent comprises carbon.

9. A process as claimed in claim 8 in which the adsorbent is selected from activated carbon and activated charcoal.

10. A process as claimed in claim 1 in which the level of adsorbent is from 0.1 to 50% by weight of the quantity of fluoromethylhexafluoroisopropyl ether in the crude composition.

11. A process as claimed in claim 1 which the crude composition is produced by contacting formaldehyde or a polymeric from thereof with hydrogen fluoride and hexafluoroisopropyl alcohol.

12. A process as claimed in claim 1 in which the crude composition is produced by reacting bis fluoromethyl ether and hexafluoroisopropyl alcohol together in the presence of an acid.

13. A process as claimed in claim 12 in which the bis(fluoromethyl) ether and the hexafluoroisopropyl alcohol are reacted together at a temperature of less than 50° C.

14. A process as claimed in claim 12 in which the bis(fluoromethyl) ether is essentially pure.

15. A process of reducing the level or removing an olefinic impurity from a composition comprising a fluorinated olefin impurity and fluoromethyl hexafluoroisopropyl ether which comprises contacting the composition with an adsorbent comprising carbon and recovering the composition depleted in the olefinic impurity.

16. A process as claimed in claim 15 in which the olefinic impurity is pentafluoroisopropenyl fluoromethyl ether.

* * * * *